(12) United States Patent
Tripathi

(10) Patent No.: US 7,416,743 B2
(45) Date of Patent: Aug. 26, 2008

(54) POLYHERBAL PREPARATION FOR THE PREVENTION OF ATHEROSCLEROSIS AND HYPERLIPIDEMIA

(75) Inventor: Yamini Bhushan Tripathi, Varanasi (IN)

(73) Assignees: Department of Biotechnology, New Delhi (IN); Banaras Hindu University, Varanasi (IN)

( * ) Notice: Subject to any disclaimer, the term of this patent is extended or adjusted under 35 U.S.C. 154(b) by 93 days.

(21) Appl. No.: 10/542,127

(22) PCT Filed: Dec. 26, 2003

(86) PCT No.: PCT/IN03/00399

§ 371 (c)(1),
(2), (4) Date: Dec. 20, 2005

(87) PCT Pub. No.: WO2004/062566

PCT Pub. Date: Jul. 29, 2004

(65) Prior Publication Data

US 2006/0147555 A1 Jul. 6, 2006

(30) Foreign Application Priority Data

Jan. 13, 2003 (IN) ........................ 1255/DEL/2002

(51) Int. Cl.
*A61K 36/00* (2006.01)
*A61K 35/56* (2006.01)
(52) U.S. Cl. ........................ 424/725; 424/547; 514/824
(58) Field of Classification Search ........................ None
See application file for complete search history.

(56) References Cited

U.S. PATENT DOCUMENTS 5,411,733 A * 5/1995 Hozumi et al. .............. 424/727

FOREIGN PATENT DOCUMENTS

| FR | 2465484 | | 4/1981 |
| IN | 200500655 | * | 3/2005 |
| IN | 200401319 | * | 4/2005 |

OTHER PUBLICATIONS

Seth et al. Indian J Physiol. Pharmacol. 1998. vol. 42, No. 1, pp. 101-106, Embase Abstract enclosed.*
Miller, A.L. Alternative Med. Review. 1998. vol. 3, No. 6, pp. 422-431, Medline Abstract enclosed.*
Mary et al. Phytomed. 2003. vol. 10, pp. 474-482.*
Tripathi et al. Inflammopharmacol. 2004. vol. 12, No. 2, pp. 131-152, Embase Abstract enclosed.*
Motlag et al. Indian J. Med. Res. 1958. vol. 46, pp. 616-625, Caplus Abstract Enclosed.*
Sigh, R.B., et al., "Hypolipidemic and antioxidant effects of Commiphora mukul adjunct to dietary therapy in patients with hypercholesterolen", Cardiovasc. Drugs Ther., vol. 8, No. 1, Aug. 1994, pp. 659-664.
J. Munasighe, T.C., et al., "Antiradical and antillipoperoxidative effects to some plant extracts used in Sri Lankan traditional medical pratitioners for cardioprotection", Phytother Res., vol. 15, No. 6 Sep. 2001, pp. 519-523.
Inflammopharmacology, vol. 12, No. 2, (2004) pp. 131-152.
Indian Journal of Experimental Biology, vol. 33, (1995), pp. 428-432.

* cited by examiner

*Primary Examiner*—Christopher R. Tate
(74) *Attorney, Agent, or Firm*—The Webb Law Firm

(57) ABSTRACT

A polyherbal preparation for the prevention of atherosclerosis and hyperlipidemia comprising a mixture of *Commiphora mukul, Boswellia serrata, Semecarpus anacardium Strychnox nux vomica, Terminalia arjuna* and *Shankha Bhasma*.

5 Claims, 2 Drawing Sheets

POLYHERBAL PREPARATION FOR THE PREVENTION OF ATHEROSCLEROSIS AND HYPERLIPIDEMIA

FIELD OF INVENTION

Figure 1:
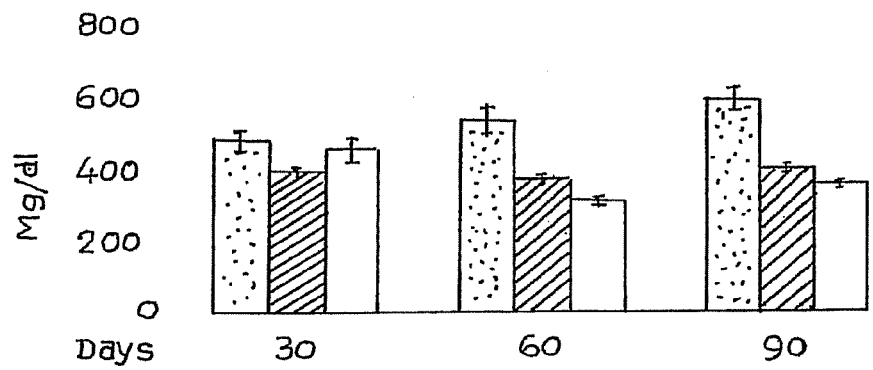
Figure 1:
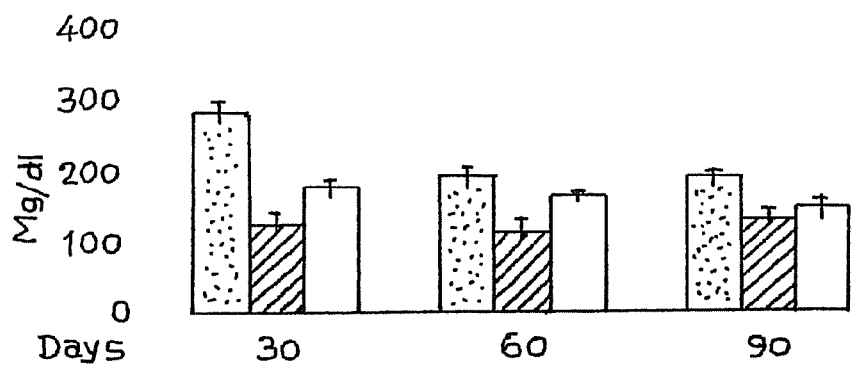
Figure 1:
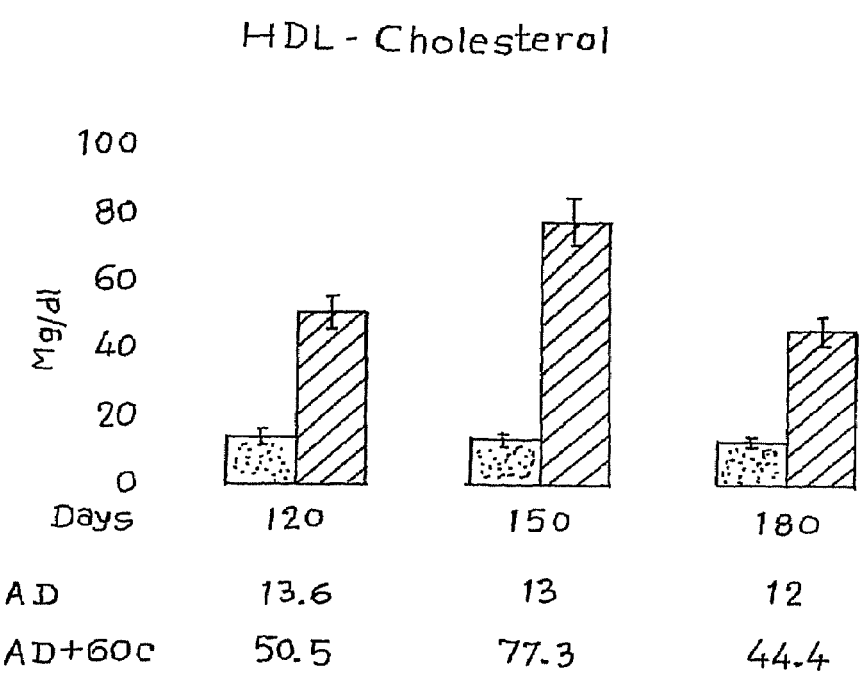

This invention relates to a novel polyherbal preparation for the prevention of Atherosclerosis and Hyperlipidemia.

BACKGROUND OF INVENTION

Atherosclerosis is one of the major problems for young age death. It is an active process of inflammation and cell proliferation. It starts when normal vascular functions go away. Basically, there is blockage in the coronary artery, which leads to the heart attack. This blockage could be due to deposition of lipid, formation of wound or sudden release of lipid from the endothelial wall due to bursting of plaque. Slow and gradual deposition of fat in the intimal layer of artery is called fatty lesion or plaque. Slowly these fatty lesions get fibrosed and calcium is deposited in it. Initially, it is a reversible process but after fibrosis, it becomes irreversible. In fact, fat deposition in the blood vessel is a natural process with aging, but in some individuals, its rate of formation is significantly high and therefore leads to pathological state of coronary artery disease.

There are several reasons for this deposition. However, the basic cause is considered to be the faulty metabolism of lipid in the body. High cholesterol diet or high level of endogenous cholesterol synthesis in the body is the basic cause of arteriosclerosis. Of course, there are several precipitating factors for this pathology, such as stress, smoking, diabetes, hypertension, age, male sex, family history leading to elevated homocystein, high serum lipoprotein-a and infection with cytomegalovirus or chlamydia. More free radical production leading to rapid oxidation of LDL, followed by the excess uptake of oxidized LDL by the macrophages leading to the formation of foam cells is the basic pathology.

PRIOR ART

As this disease is multi-factorial, there are several approaches to manage artherosclerosis. First and foremost, it is to reduce the lipid load in the body to or to increase the HDL content or to reduce the burden of free radicals and oxidized LDL or to remove foam cells and fatty lesions. There are two major steps, (a) Prevention of the formation of fatty plaque; (b) Regression of plaque already formed. At present, there are two main approaches for the management of atherosclerosis (1) Invasive techniques; and (2) Non-invasive techniques. In the non-invasive group of techniques, the most prominent approach is to lower the blood lipid, specially the cholesterol and triglycerides. In this approach, the main pathway is to inhibit the endogenous cholesterol synthesis by blocking the HMG-Co synthase. A drug known is different kind of Statins. In this way, there is reverse cholesterol transport from the tissue to the blood leading to the lowering of the LDL and VLDL. Several medicinal plants products are also available with a hypolipidemic claims, eg. *Commiphora mukul, Terminalia arjuna, Acorus calamus*, etc. In fact ayurvedic literature discloses such plant names, but not much scientific study has been made with these plants.

Yet another approach is to increase the HDL in the blood. Unfortunately, there is no good medicines which can increase the serum HDL, The exercise is the only way to achieve this goal. Use of cow butter/milk has also shown the property of raising serum HDL upto some extent, but it can not be used as a medicine in the patients of hyperlipidemia and artheroscle-rosis.

Third approach is to prevent the oxidation of LDL in the blood, because ox LDL is the basic cause of foam cell formation and thereafter its deposition in the arterial wall, forming arteriosclerotic plaque. To achieve this goal, antioxidants are being recommended as the diet supplements. Although the use of antioxidants has increased significantly as a diet supplement in the management of artherosclerosis and other coronary artery diseases, but does not fall in the group of therapeutic medicine, because of its non-specific role. Metal chelaters are also used to prevent the formation of free radicals, because iron mediated Fenton's reaction is one the basic cause of hydroxyl radical production.

After knowing the molecular pathway of atheroma formation, gene therapy is being tried in the management of this disease. It is reported that stable atheroma is not as dangerous as the unstable one. For this unstability, a group of proteases known as MMPs (Matrix Metallo proteinases) are responsible. In fact, they digest the fibrous cap of the plaque and allow the lipid to come out of the plaque and block the arterial blood flow.

Attempts are now being made to introduce the genes to inhibit these MMPs. Similarly, the most recent approach of gene therapy is to inhibit a growth factor M-CSF (Macrophage colony stimulating factor), which is responsible for the proliferation of smooth muscle cells and rapid formation of foam cell leading to their deposition.

One more approach to manage artherosclerosis is to regulate the inflammatory cytokines and various enzymes like lipoxygenase and cyclooxygenase, because inflammation is one of the basic factors, responsible for plaque formation.

Since artherosclerosis is a multiethiological factor disease, so doctors recommend a series of medicine to manage this disease and still the disease is not manageable because of uncoordinated approach. However, there is no medicine which can target several etiological factors simultaneously by giving one tablet. The patient is supposed to take several medicines in a day, which gives him a kind of psychological depression. These medicines, when given in isolation does not give significant impact on the prevention of atheromafor-mation, because other factors become more prominent. The genetherapy, which is being developed is at the infancy stage and if at all, it comes to the public use, it will be very expensive and also with several side effects, only the time will tell for its success.

There are many claims to prevent the formation of plaque, by reducing the risk factors, by taking more antioxidants or by lowering the cholesterol by the use of several hypolipidemic drugs like Statins, etc. Once atheroma is detected, the coronary bypass, etc. are the only remedies. In fact, no good drug is available to regress the plaque, already formed.

OBJECTS OF THE INVENTION

An object of this invention is to propose a novel polyherbal preparation which has the capacity to target several etiological pathways, and finally lead to atherosclerosis.

Another object of this invention is to propose a novel polyherbal preparation which is anti-inflammatory anti oxidant and increases serum HDL, and more specifically, it inhibits Lox-15, Cox-2 and Ca-deposition in the plaque, increases Collagen in the chronic plaques, increases serum HDL and decreases serum TG.

Still another object of this invention is to propose a novel polyherbal preparation which enhances serum HDL and prevents plaque formation even in the presence of high-serum lipid.

Yet another object of this invention is to propose a novel polyherbal preparation which enhances the collagen tissue in the old plaque indicating towards the stabilization of the plaque.

A further object of this invention is to propose a novel polyherbal preparation which inhibits the Cyclooxygenase-2 and lipoxygenase-15, which are responsible for atherosclerosis.

A still further object of this invention is to propose a novel polyherbal preparation which is cost-effective, more effective than its component medicinal plant and does not have any toxic or side effect with high therapeutic safety margin.

DESCRIPTION OF INVENTION

According to this invention, there is provided a polyherbal preparation for the prevention of atherosclerosis and hyperlipidemia comprising a mixture of *Commiphora mukul, Bosewellia serrata, Semecarpus anacardium Strychnos nux vomica, Terminalia arjuna* and *Shankha Bhasma*.

The polyherbal composition may further include *Rubia cordifolia, Bacopa monnieri, Triphala* and *Trikatu*.

In accordance with this invention, the constituents are present in the following ratio:

| | |
|---|---|
| Purified Commiphora mukul | 1 to 4 |
| Pure Boswellia serrata | 0.5 to 4 |
| Purified Semecarpus anacardium | 0.1 to 0.4 |
| Purified powder Strychnos nux vomica | 0.4 to 2 |
| Pure powder of water extract Termenalia arjuna | 0.3 to 2 |
| Shankha Bhusma | 0.5 to 2 |

Further, any one or more of the following constituents are added in the following ratio:

| | |
|---|---|
| Rubia cordifolia | 0.05 to 1 |
| or Bacopa monnieri | 0.5 to 3 |
| or Triphala | 0.5 to 3 |
| and Trikatu | 0.5 to 3 |
| Specifically, an advantageous ratio is: | |
| Purified Commiphora mukul | 3.7 |
| Pure Boswellia serrata | 3.0 |
| Purified Semecarpus anacardium | 0.1 |
| Purified powder Strychnos nux vomica | 1.0 |
| Pure powder-water extract Termenalia arjuna bark | 0.7 |
| Shankha Bhusma | 1.5 |

EXAMPLE

Composition of Atherogenic Diet:

Antherogenic diet consists of cholesterol rich-rabbit chow, cabbage and gram in the same amount as in control rabbits. Atherogenic diet is made as follows:

The chow is powdered and mixed with the following items in a specific ratio as given below and again pellet is made. It is dried in oven and kept in refrigerator. At one time, diet was prepared only for 4 days.

Composition of Diet:

| | |
|---|---|
| Rabbit chow | 57% |
| Milk powder | 14% |
| Yeast powder | 04% |
| Salt | 01% |
| Multivitamin | 0.1% |
| Cholesterol | 05% |
| Hydrogenated fat | 17% |
| Cholic acid | 01% |

Experimental Details:

Male rabbits were randomly divided into 3 groups, having 12 animals in each. They were kept for 15 days for acclimatization in the laboratory condition. During this period, deworming was done to each animal and Hostacycline and Vimeral was given in drinking water. The animals were divided into the following groups;

Control diet (CD)

Atherogenic diet (AD)

Atherogenic diet—BHUx 60 mg/100 g body weight ($AD_{40}$)

Control diet consists of rabbit chow, cabbage and gram 400 g/day and water ad libitum.

Atherogenic diet was given to the rabbits in the control group, 3 months later, BHUx was given in the experimental group along with the atherogenic diet for another 3 months. Therefore, total duration of the experiment was of 6 months. After every one month, lipid profile was carried out in blood and at the end of experiment, animal was sacrificed and heart, liver, kidney, dorsal aorta were saved. These tissues were processed for histological studies. Sections of 5 micron thickness were cut and stained with different stains. In the AD groups (Experimental control) only 2 ml of gum acacia suspension in distilled water (5%) was given in the similar way. Lipip profile was carried out by using Zydus Pathline kits (a croup and Cadila Healthcare Ltd.) in terms of cholesterol, TG, LDL and HDL. After 3 months, animals were sacrificed to collect heart and dorsal aorta.

(A) Histology:

(1) Study with Dorsal Aorta—It was separated from the heart at the point of aortic arch origin and longitudinally cut open. It was stained in Sudan IV stain. After making a tracing of the atherogenic patches, the tissue was fixed and processed for block preparation and section cutting.

(2) Study with aortic arch and coronary artery—Whole heart was divided into 2 parts, named $H_1$ and $H_2$. The upper $H_1$ part was cut at 6 u thickness and stained with Hematoxylin and Eosin (H&E). Microscopic study was made in the region of aortic arch and coronary artery with reference to intimal thickening. These sections were separately stained with specific stains for the vistalization of collagen tissue and calcium deposition.

(3) Study with kidney and liver—Sections were stained with H & E and with AgNO3 separately to evaluate the degree of fibrosis to and necrosis.

(B) Biochemical tests—Blood of each animal was selected and plasma/serum was isolated as per need to assay SGOT, SGPT, Alkaline phosphatase and complete lipid profile.

(C) In vitor assay—To study the effect of the preparation of the present invention on cyclooxygenase and lipoxygenase, in vitro enzyme assay was carried out by using standard oxygraph technique. The results show that the preparation of the present invention is more sensitive to Cox-2 inhibition than the Cox-1. Similarly, on Lipoxygenase assay, it showed high sensitivity to the 15-Lipoxygenase than the other isoenzymes.

BRIEF DESCRIPTION OF THE ACCOMPANYING DRAWINGS AND TABLES RELATED TO RESULT

FIG. 1: Bar diagram showing lipid profile with raised HDL.

What is claimed is:

1. A polyherbal preparation for treating and/or reducing the risk of atherosclerosis and hyperlipidemia comprising an effective amount of a mixture of *Commiphora mukul, Boswellia serrata, Semecarpus anacardium, Strychnos nux vomica, Terminalia arjuna* and *Shankha Bhasma*.

2. A polyherbal preparation as claimed in claim 1 wherein *Commiphora mukul, Boswellia serrata, Semecarpus anacardium Strychnos nux vomica, Terminalia arjuna* and *Shankha Bhasma* are present in the following ratio:

| | |
|---|---|
| Purified *Commiphora mukul* | 1 to 4 |
| Pure *Boswellia serrata* | 0.5 to 4 |
| Purified *Semecarpus anacardium* | 0.1 to 0.4 |
| Purified powder of *Strychnos nux vomica* | 0.4 to 2 |
| Pure powder of water extract of *Terminalia arjuna* | 0.3 to 2 |
| Shankha Bhusma | 0.5 to 2. |

3. A polyherbal preparation as claimed in claim 1 further comprising *Rubia cordifolia, Bacopa monnieri, Triphala* and *Trikatu*.

4. A polyherbal preparation as claimed in claim 3 wherein *Rubia cordifolia, Bacopa monnieri, Triphala* and *Trikatu* are added in the following ratio:

| | |
|---|---|
| *Rubia cordifolia* | 0.05 to 1 |
| or *Bacopa monnieri* | 0.5 to 3 |
| or *Triphala* | 0.5 to 3 |
| and *Trikatu* | 0.5 to 3. |

5. A polyherbal preparation as claimed in claim 1 wherein *Commiphora mukul, Boswellia serrata, Semecarpus anacardium, Strychnos nux vomica, Terminalia arjuna* and *Shankha Bhasma* are present in the ratio of:

| | |
|---|---|
| Purified *Commiphora mukul* | 3.7 |
| Pure *Boswellia serrata* | 3.0 |
| Purified *Semecarpus anacardium* | 0.1 |
| Purified powder of *Strychnos nux vomica* | 1.0 |
| Pure powder of water extract of *Terminalia arjuna* bark | 0.7 |
| Shankha Bhusma | 1.5. |

* * * * *

UNITED STATES PATENT AND TRADEMARK OFFICE
CERTIFICATE OF CORRECTION

| | |
|---|---|
| PATENT NO. | : 7,416,743 B2 |
| APPLICATION NO. | : 10/542127 |
| DATED | : August 26, 2008 |
| INVENTOR(S) | : Tripathi |

Page 1 of 1

It is certified that error appears in the above-identified patent and that said Letters Patent is hereby corrected as shown below:

Column 5, Line 23, Claim 2, "*Shankha Bhusma*" should read -- *Shankha Bhasma* --

Column 6, Line 24, Claim 5, "*Shankha Bhusma*" should read -- *Shankha Bhasma* --

Signed and Sealed this

Thirteenth Day of January, 2009

JON W. DUDAS
*Director of the United States Patent and Trademark Office*